United States Patent [19]

Lane

[11] Patent Number: 5,037,434

[45] Date of Patent: Aug. 6, 1991

[54] BIOPROSTHETIC HEART VALVE WITH ELASTIC COMMISSURES

[75] Inventor: Ernest Lane, Huntington Beach, Calif.

[73] Assignee: Carbomedics, Inc., Angleton, Tex.

[21] Appl. No.: 508,275

[22] Filed: Apr. 11, 1990

[51] Int. Cl.$^5$ .............................................. A61F 2/24
[52] U.S. Cl. ......................................... 623/2; 623/900
[58] Field of Search .................................... 623/2, 900

[56] References Cited

U.S. PATENT DOCUMENTS

| | | | |
|---|---|---|---|
| 4,084,268 | 4/1978 | Ionescu et al. | 623/900 |
| 4,106,129 | 8/1978 | Carpentier et al. | 623/2 |
| 4,192,020 | 3/1980 | Davis et al. | 623/900 |
| 4,343,048 | 8/1982 | Ross et al. | 623/2 |
| 4,778,461 | 10/1988 | Pietsch et al. | 623/2 |
| 4,888,010 | 12/1989 | Bokros | 623/2 |

Primary Examiner—Randy Citrin Shay
Attorney, Agent, or Firm—John R. Merkling

[57] ABSTRACT

A bioprosthetic heart valve comprising first and second mechanisms for supporting leaflets to provide multiple effective spring constants. An inner frame supporting commissures of the valve is elastic, permitting the commissures to bend in toward the center of the prosthetic heart valve at very low loads. A relatively rigid annular support ring supports the elastic frame and provides the second spring constant mechanism. An attachment system for sewing bioprosthetic leaflets to the frame and clamping the leaflets between the frame and the annular ring minimizes stress risers in the leaflets. The leaflets have an uncoupled mating edge where the leaflets meet in the center of the valve. The uncoupled portions of the leaflets permit the leaflets to roll by each other.

20 Claims, 5 Drawing Sheets

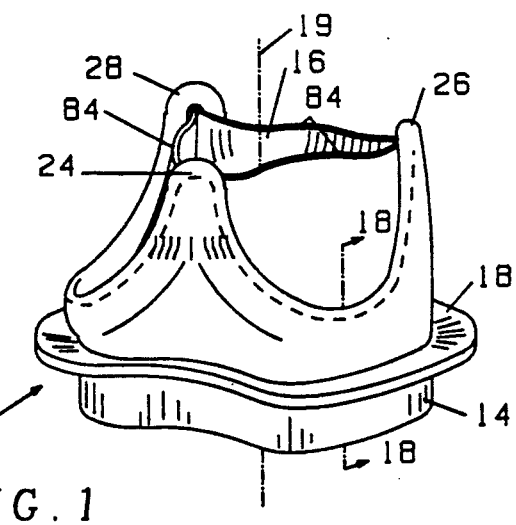
FIG. 1
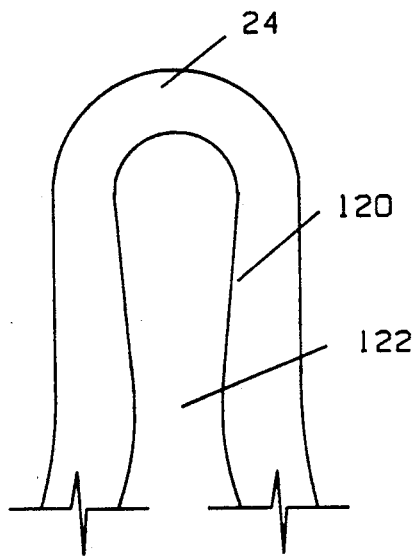
FIG. 20
FIG. 21
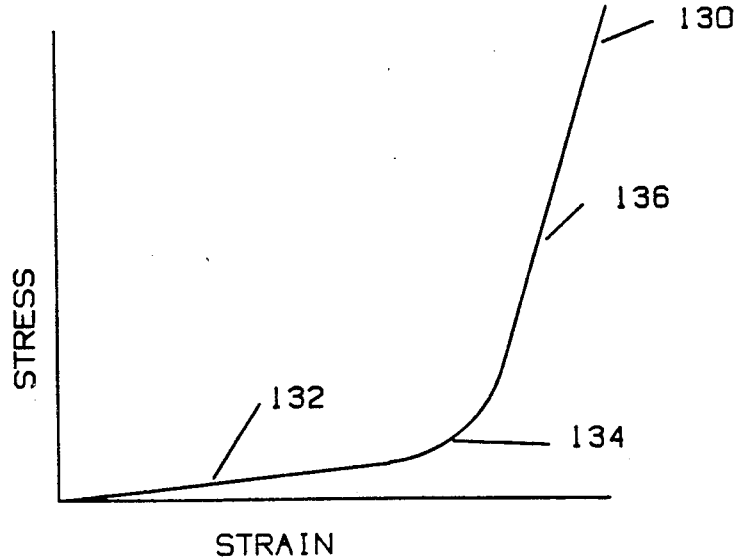

BIOPROSTHETIC HEART VALVE WITH ELASTIC COMMISSURES

BACKGROUND OF THE INVENTION

Prosthetic heart valves, used to replace diseased natural heart valves, fall generally into two categories. The first category comprises heart valves with relatively rigid leaflets. These valves have one, two or three leaflets formed of a stiff biocompatible substance, such as pyrolitic carbon. The valves are often designed to have two leaflets pivoting in a rigid annulus, such as the design shown in U.S. Pat. No. 4,888,010 to Bokros.

The second category of prosthetic heart valves, called herein bioprosthetic valves, comprises valves with flexible leaflets, frequently of a biological material. This second category can also be divided broadly into two classes. The first class comprises bioprosthetic heart valves typically including a wire frame with three flexible leaflets attached thereto. Examples of such valves are shown in Carpentier, et al., U.S. Pat. No. 4,106,129, Ionescu, et al., U.S. Pat. No. 4,084,268 and Davis, et al., U.S. Pat. No. 4,192,020. These heart valves imitate the natural action of heart valves and so provide a structure which is relatively compatible with the cardiovascular system. However, they are still prosthetic devices, and are subject to wear and fatigue. There is a continuing need to improve the long-term durability of bioprosthetic valves.

Prior valves, such as the valve described in Carpentier, U.S. Pat. No. 4,106,129, comprise wire frames, usually of circular cross-section with three commissures supporting three leaflets. The wire frame could be flexible, but not elastic, because the commissures are relatively rigid. As the valve leaflets move from open to closed positions, bending stresses occur in the portion of the wire frame connecting the commissures. The commissures themselves do not bend significantly. An attempt to overcome the limitations of wire frame valves was proposed by Ross, et al. U.S. Pat. No. 4,343,048. Ross taught that the commissures should be flexible along substantially their entire length, bending in the manner of a fishing pole.

The second class of bioprosthetic heart valves do not have a stent or frame. They have the advantage of being constructed from flexible material, but they can be collapsed and deformed by the action of the heart. The action of the heart muscles on this type of valve can fold the valve material and create unexpected stress risers which can eventually lead to failure.

SUMMARY OF THE INVENTION

In my invention, I have combined the advantages of the first and second classes of bioprosthetic heart valves, as I have described them above, to produce a valve which has a stress-strain curve similar to that of normal tissue, but which also has a relatively rigid outer frame to prevent deformation of the valve. Most living tissue has a stress-strain curve which are substantially different from the stress-strain curves of non-biologic materials or non-living biologic materials. At low to moderate strains, there is little stress in the material which tends to give or yield readily. At some intermediate level the relation changes sharply, and stress rapidly increases. The biologic structure resists further deformation. This characteristic can be experienced, for example, by pulling on one's earlobe. The lobe will easily stretch in tension to a certain extension, after which further stretching is limited. The same characteristics apply to tissues of natural heart valves.

I have invented a bioprosthetic heart valve which incorporates this characteristic. As the valve begins to close, there is very little resistance to radial motion in leaflets of the valve. As the valve closes, however, a secondary mechanism for supporting the leaflets takes over and the stress in the leaflets increases relatively rapidly as the leaflets come to a closed position. I have been able to pattern the action of the valve on this stress-strain characteristic of living biologic tissue by using two mechanisms in the supporting structure of the valve. In addition the structure of my design achieves the flexibility characteristic of stentless bioprosthetic valves combined with a rigid annular ring which prevents the valve from folding in undesirable ways.

In my invention, an inner frame supporting the commissures of a valve is elastic, permitting the commissures to bend in toward the center of the prosthetic heart valve at very low loads, thus distributing the necessary strains and resulting stresses. The inner frame alone has a spring constant of about 3 gm/mm. The frame comprises a flat ribbon rather than a round wire and is, consequently, substantially more elastic in a direction perpendicular to a wide side of the ribbon than in a direction perpendicular to a narrow side of the ribbon. Leaflets supported by the frame can move easily in a radial direction, but their motion is otherwise controlled by the frame. To support the very elastic frame, I have designed a relatively rigid annular support ring. I have also invented an attachment system for sewing bioprosthetic leaflets to the frame and clamping the leaflets between the frame and the annular ring to minimize stress risers in the leaflets. Stress in the leaflets cannot be eliminated, but wear and the possibility of failure can be reduced if the stresses are relatively uniformly distributed. The support ring has commissure supports which extend to about fifty-five to sixty-five percent of the height of the commissures of the frame.

The frame is attached to the ring at adjacent upper edges. In the lower thirty to forty percent of the frame adjacent the ring, the rigid ring prevents the frame from bending in its lower portion, but the attachment mechanism permits the frame to shift circumferentially to relieve minor stress concentrations. When the valve of my invention begins to close, the leaflets will be displaced with little stress, just as living tissure tends to have an initial regime of large strain for low stress. About midway through closure the attachment system begins to transfer the load in the leaflets to the annular support ring. The effective stress-strain curve for the valve changes and the slope of that curve becomes steep, as is characteristic of living tissue. Thus, the inner stent is not permitted to flex elastically along its entire length, but can only flex in the upper portion. The rigid ring supports most of the loads during the latter stages of closing and when the valve is closed. When the valve is closed, the stresses are distributed throughout the frame and the annular support ring. Consequently, a lower maximum level of stress can be expected.

Between the secondary commissures, the support ring is splayed outward in an ogive shape. This shape reduces the possibility of tissue abrasion during valve opening in the aortic position. In addition, it serves as a suture guard inhibiting puncture of the leaflets during implantation. The ogive also helps to shift the more bulky structures of the valve into the sinus of valsalva for better hemodynamic performance when the valve is in the aortic position.

I have also invented a leaflet with an uncoupled mating edge where the leaflets meet in the center of the valve. By uncoupled, I mean that there is no tensile stress carried through that portion of the leaflet from one commissure to an adjacent commissure of the valve. As the valve opens and closes, the uncoupled portions of the leaflets will permit the leaflets to roll by each other.

With the foregoing in mind, it is a principal object of my invention to provide a bioprosthetic heart valve which has an effective stress-strain curve similar to a curve characteristic of living biologic tissue.

Another important object of my invention is to provide a bioprosthetic heart valve with a frame confined by a relatively rigid annular ring such that the frame flexes only in an upper portion thereof.

It is also a principal object to provide a heart valve with a first means for supporting the leaflets with low resistance to radial displacement during a first part of a closing cycle and with a second means for supporting the leaflets with a relatively high resistance to radial displacement during a second part of the closing cycle.

It is also an object of my invention to provide a structure for sewing leaflets into a bioprosthetic heart valve which minimizes stress risers in the leaflets.

Another important object of my invention is to provide a bioprosthetic heart valve structure which clamps the leaflets between the frame and the annular ring.

A further principal object of my invention is to provide improved leaflets with an uncoupled mating edge.

Another object of my invention is to provide a commissure with a canting feature to minimize torsional loading on the leaflets adjacent the commissures.

These and other objects and features of my invention will be apparent from the following detailed description taken with reference to the accompanying drawings.

BRIEF DESCRIPTION OF THE DRAWINGS

FIG. 1 is a perspective view of a bioprosthetic heart valve according to my present invention.

FIG. 20 is an enlarged plan view of a commissure of the frame.

FIG. 21 is a stress-strain curve.

DESCRIPTION OF THE PREFERRED EMBODIMENT

Figure 2:
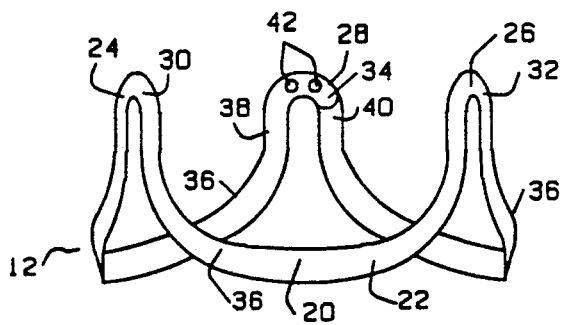
FIG. 2 is a plan view of an elastic frame.

I will now explain my invention with reference to the accompanying drawings, wherein like numerals designate like parts throughout.

FIG. 1 shows a bioprosthetic heart valve 10 which comprises a frame 12 (FIG. 2), an annular support ring 14 (FIG. 5), three identical leaflets 16 and a suture ring 18. The valve 10 is generally symmetrical around an axis 19, which is parallel to the expected flow of blood through the valve. In the illustrated embodiment, the suture ring 18 is scalloped, and, accordingly, the bioprosthetic heart valve 10 is configured for implantation for an aortic heart valve. This, however, is merely illustrative since the features of this invention are equally applicable to other heart valves which could employee suture rings of other configurations.

As shown in FIG. 2, the frame 12 comprises a flat ribbon 20. The ribbon 20 is formed by stamping or cutting a pattern out of a flat sheet of biocompatible material. I prefer Elgiloy, which is a trademarked cobalt-nickel-chromium alloy produced by Elgiloy Company. When wrapped end to end, the ribbon 20 forms an annular structure with a wide dimension 22 generally aligned parallel to the expected flow of blood through the valve 10. The ribbon 20 forms three commissures 24, 26, 28 symmetrically spaced around the axis 19 of the valve, and equidistance from each other. Each commissure 24-28 comprises a semicircular tip 30, 32, 34 respectively. Each semicircular tip 30-34 is connected to an adjacent tip by a curved segment 36. When the ribbon 22 is in an annular configuration, as shown in FIG. 2, the curved connecting portions 36 appear semicircular. In order to achieve this structure, the ribbon is stamped out of the Elgiloy sheet with a curved pattern which is empirically derived and shown generally in FIG. 19. Two ends 38, 40 of the ribbon are joined at one of the tips 34 by overlapping the ends 38, 40 and resistance welding 42 the ends together.

The ribbon should be at least ten times wider than it is thick. In the preferred embodiment of my invention, the ribbon 20 is about twenty times wider than it is thick. Consequently, the frame 12 is very elastic. The commissures 24-28 can easily bend in toward the axis of the valve. This flexing takes place in the upper one-half to two-thirds of the height of the frame. A radial force directed inward toward the axis of the valve at the tips of the commissures tends to immediately bow the commissures. This action is distinguishable from the action of prior art valves, for example, U.S. Pat. No. 4,106,129, of which I was a co-inventor. In the '129 valve, the commissures were relatively rigid in the radial direction. The commissures could, therefore, be expected to remain aligned with the axis of the valve until shortly before the valve was fully closed. As the valve fully closed, the leaflets applied a moment load to the commissures and the commissures bent in toward the center of the valve by bending in the connecting portions between the commissures. The commissures themselves would remain relatively straight with deflection occurring at the base of the commissures. This action tended to spring-load the leaflets and put a particularly high stress area near the tips of the commissures, the point of greatest lever-arm in bending. This not only created unwanted stress risers in the leaflets and in particular at edges of the leaflets, but it also created a whip-lash effect before the valve began to open. Under the influence of the spring force at the commissures, the leaflets tended to snap open, with associated high impulse stresses in the valve structure or leaflets.

Figure 3:
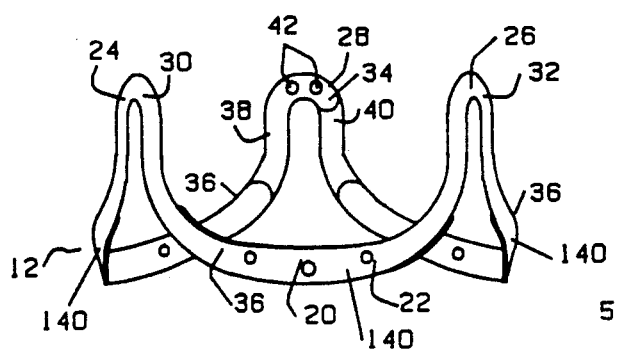
FIG. 3 is a plan view of an alternative embodiment of the frame of FIG. 2 with stiffening ribs.
Figure 4:
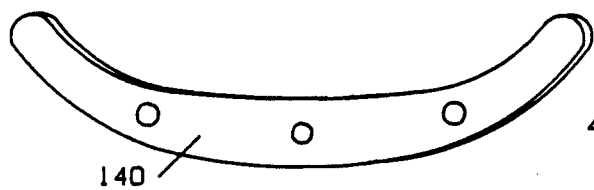
FIG. 4 is a perspective view of a stiffening rib.

In contrast, an elastic action in the commissures allows the commissure to bend uniformly in the upper portion of its length. The frame stress is not concentrated at the tip of the commissure, but is distributed more uniformly along the bent portion of the commissure. This distribution of frame stress reduces the maximum stress carried by any portion of the leaflet. Furthermore, the leaflets can roll open and a very low spring energy stored in the frame when the valve was closed can be recovered more smoothly as the valve opens. This eliminates a snapping action and associated high momentary stresses which can occur in leaflets supported by flexible stents, where the spring action is concentrated in the connecting portion of the frame. However, the frame is attached to the ring at adjacent upper edges. In the lower thirty to forty percent of the frame, the rigid ring prevents the frame from bending in its lower portion, but the attachment mechanism permits the frame to shift circumferentially to relieve minor stress concentrations. Thus, the inner stent is not permitted to flex elastically along its entire length, but can only flex in the upper portion. The ring frame carries most of the loads during the latter stages of closing and when the valve is closed. In an alternative embodiment, shown in FIG. 3, I have provided stiffening ribs 140 which further restrict movements to the upper portion of the frame 12. The ribs can be secured to the frame by sewing or welding. Locations for three spot welds for each rib are shown in FIG. 3 and FIG. 4. The ribs may be formed of Elgiloy on the order of 0.008 inches in thickness or of wire. The ribs stiffen the lower third of the height of the frame, thus contributing to the transfer of load from the frame 12 to the ring 14, as I will explain below. The same effect, however, can be achieved by proper attachment of the frame to the ring, in the manner described herein.

The commissures of the frame 12 have an extremely low spring constant in the radial direction. The spring constant of my frame alone is approximately 3 gm/mm. As the valve begins to open, therefore, the leaflets can move quite readily in a radial direction, although they would still be constrained circumferentially. As I will explain more fully below, this contributes to an effective stress-strain relationship in the leaflets which approximates that of living tissue.

The flattened shaped of the ribbon 22 gives the frame 20 the desired radial elasticity so that the commissures 24–28 can flex toward the axis of the valve. At the same time, the frame 20 is relatively stiff circumferentially so that the bending of the commissures will be constrained to a radial direction. The frame alone can easily be deformed because of its great elasticity. To maintain the over all annular shape of the valve 10, the relatively rigid annular ring 14 is needed.

Figure 7:
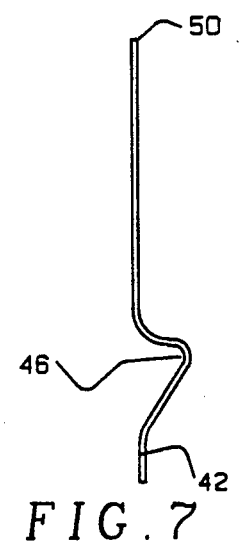
FIG. 7 is a through section of the annular ring taken along line 7—7 of FIG. 6.
Figure 6:
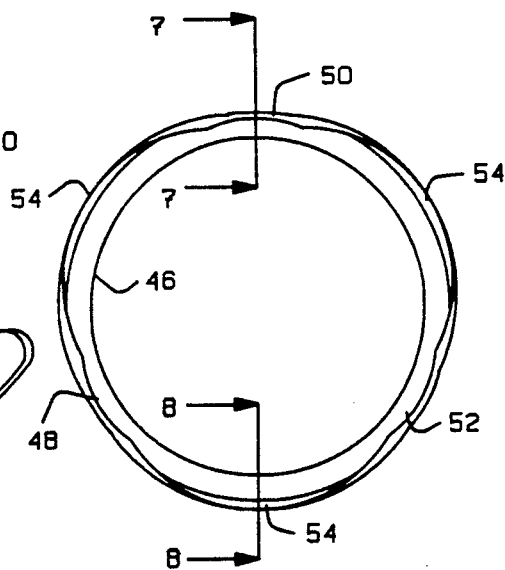
FIG. 6 is a top view of the ring of FIG. 5.
Figure 5:
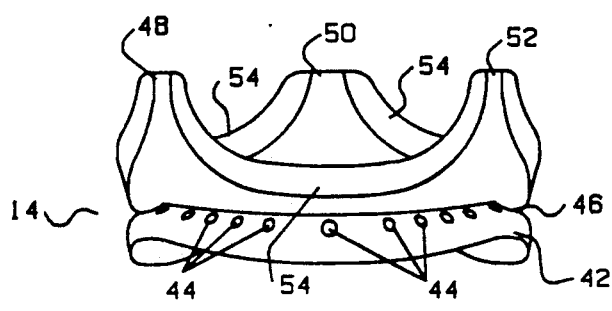
FIG. 5 is a plan view of an inflexible annular ring for supporting the frame of FIG. 2.
Figure 8:
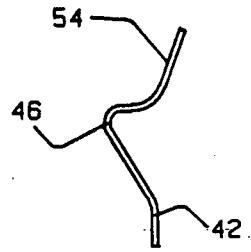
FIG. 8 is a through section of the annular ring taken along line 8—8 of FIG. 6.
Figure 16:
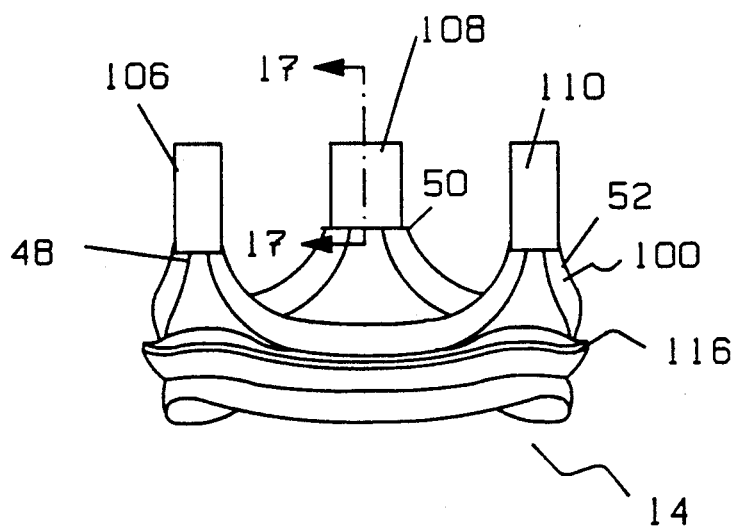
FIG. 16 is a plan view of the annular ring with covering and suture ring.

As seen in FIGS. 5 and 6, the support ring 14 comprises an annular base 42 having a plurality of sewing holes 44 placed uniformly around the support ring 14 in a circumferential groove 46. Above the groove 46 are three commissure supports 48, 50 and 52 which are spaced equidistant from each other and are adapted to cooperate with the three commissures 24–28 of the frame 12. The commissure supports cover about fifty-five to sixty-five percent of the axial height of the commissures. Between adjacent commissure supports there is a channel 54 into which a portion of each connecting part 36 of the frame 12 can be fitted when the valve 10 is assembled. As can be seen in FIG. 7, the commissure supports are substantially parallel to the axis 19 of the valve 10. Between the commissure supports, however, the channel 54 is inclined out away from the axis of the valve 10, as shown in FIG. 8. This outward inclination between the commissure supports forms an ogive segment in the ring. The outward configuration tends to reduce the possiblity of abrasion to the tissue during valve opening in the aortic position. In addition, it provides a suture guard so as to reduce the possibility of puncturing the tissue leaflets during implantation of the valve. The configuration shown permits the sewing ring 18 to be attached to the valve relatively far away from the commissures thus shifting most of the structure of the valve into the sinus of valsalva for better hydrodynamic performance when the valve is in the aortic position.

Figure 10:
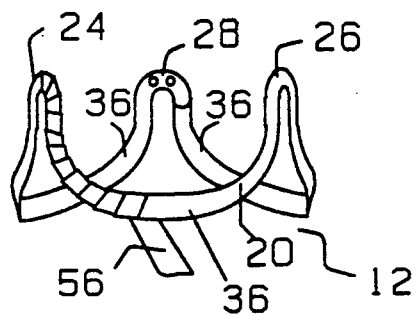
FIG. 10 is a plan view of the frame, showing installation of wrapping.
Figure 11:
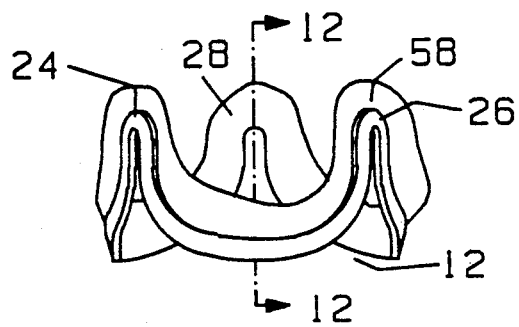
FIG. 11 is a plan view of the frame showing installation of cloth covering.
Figure 12:
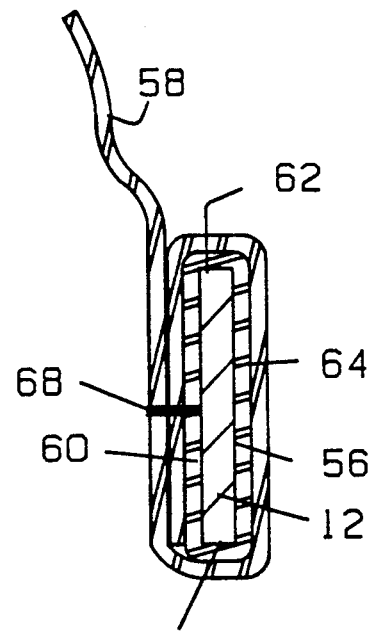
FIG. 12 is a through section of the frame taken along line 12—12 of FIG. 11.

FIG. 10 shows a ribbon 56 wrapped around the Elgiloy frame 12 to cushion the frame. In my preferred embodiment, the ribbon 56 is a seamless tubular cloth. It may also be made of a non-woven or spunbonded polyester material, for example, Reemay (trademark), a material available from Dupont. With the ribbon 56 wrapped around the frame 12, the surface of the ribbon can be smoothed and adjusted using a heating device. The ribbon 56 both cushions the frame 12 and stabilizes other material which is attached to the frame. After the ribbon has been wound on the frame, a seamless tubular cloth or a flat bias cut cloth 58, shown in FIG. 11, is placed on the frame 12. A suitable material is Dacron (trademark) USCI surgical fabric. As seen in FIG. 12, the tubular cloth 58 is wrapped from an inside 60 of the frame up over a top 62 of the frame, around an outside 64, under a bottom 66, and back up the inside 60 of the frame. Then the cloth 58 is stitched 68 together with the ribbon 56 on the inside 60 of the frame 12.

Figure 13:
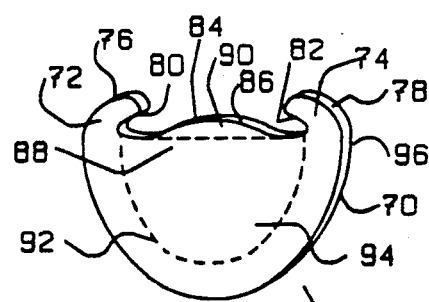
FIG. 13 is a perspective view of a leaflet.

The leaflets 16 are cut from a flat sheet of biocompatible material in a shape shown in FIG. 13. I prefer to use bovine pericardial tissue, but other biocompatible materials may be used, such as other biological tissue or a synthetic material such as film polyurethane. The leaflets 16 comprise an arcuate outer edge 70 which terminates at two ears 72, 74. The ears 72, 74 are mirror images of each other and comprise a semicircular upper edge, 76, 78 respectively, and a linear lower edge, 80, 82 respectively. The two linear edges 80, 82 are connected by a free edge 84. The junction between the linear edges and the free edge are filletted to distribute stress. In the bioprosthetic heart valve 10, the free edge 84 connects two adjacent commissures of the valve 10 and is the edge which mates with portions of the adjacent leaflets when the valve 10 is closed. A portion 86 of the free edge 84 is curved above a line 88 connecting the two junctions between the linear segments 80, 82 and the free edge 84. In the operation of my valve, tensile stresses can occur in the leaflet 16 between any two points attached to the frame 12. The line 88 represents the maximum extent of tensile forces in the leaflets 16. In the portion 90 of the leaflet between the line 88 and the curved portion 86 of the free edge 84, therefore, there will be no tensile forces from the frame. The portion 90 will be uncoupled from the frame and free to flex in directions perpendicular to the leaflet 16. As the leaflets open and close, the unconnected portions 90 of each leaflet will be able to roll past each other without binding and without undue stress in the leaflets or the valve itself. When the valve is closed, the uncoupled portion permits the three leaflets 16 to fit more closely together and minimize regurgitation and wear.

Figure 14:
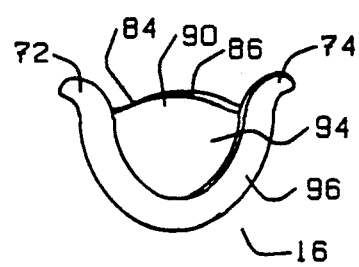
FIG. 14 is a perspective view of the leaflet of FIG. 13 with a folded outer edge.

To attach the leaflets 16, the arcuate edge 70 is foled along a curve, such as the dotted line 92, substantially equidistant from the arcuate edge 70 and connecting the ends of the flat segments 80, 82. If bovine pericardial tissue or a similar substance is employed in the leaflets 16 there will usually be a smooth side 94 and a rough side 96. The arcuate edge 70 should folded be toward the smooth side 94, as shown in FIG. 14. This causes the ears 72, 74 to be directed out from the leaflet 16. The leaflets 16 are then placed on the wrapped frame 12 as shown in FIG. 15, and both the arcuate edge 70 and the semicircular edge 76 of the ears are stitched to the bias cut cloth 58 and to the ribbon 56 near the upper edge 62 of the frame 12.

I have also found that stress in the leaflets can be reduced by providing a canted tip in the commissures. By canted tip, I mean the structure illustrated in FIG. 20. Near a commissure tip 24, an inside edge 120 forms a slightly narrowed opening 122 for the commissure. This produces an area on the inside of the commissure which has a slight upward "V" shape. When the leaflets are open, the upper edge 84 of the leaflet, where the leaflet contacts the commissure, will be pressed against the inside edge 120 of the commissure along one side of the "V" portion and away from the adjacent leaflet. As the valve closes, the adjacent leaflets will be able to roll towards one another and away from the edge 120 of the commissure. This action tend to minimize the torsional loading on the tissue of the valves immediately adjacent the commissures.

Figure 17:
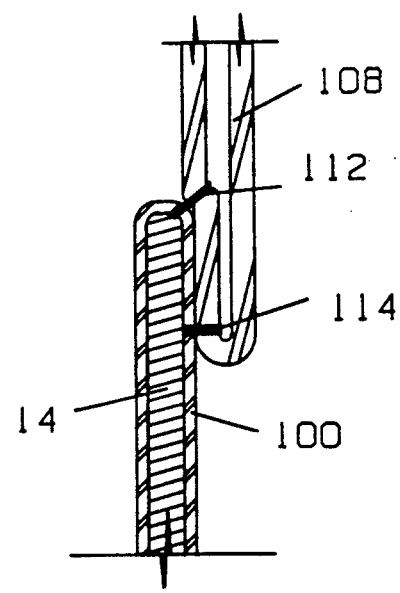
FIG. 17 is a through section of a portion of the ring and covering taken along line 17—17 of FIG. 16.
Figure 9:
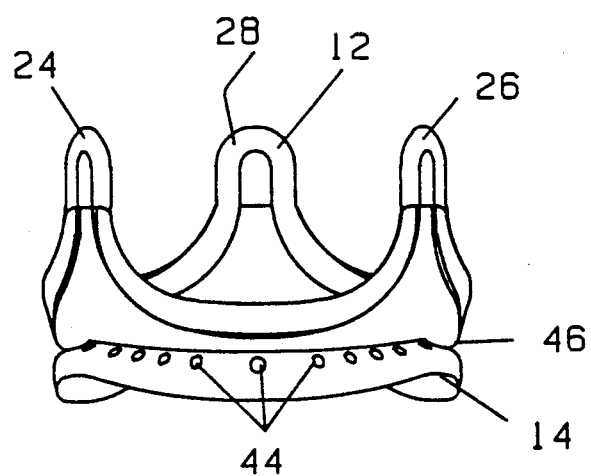
FIG. 9 is a plan view of the frame and annular ring, without other structure, showing the relationship between the frame and the annular ring.
Figure 15:
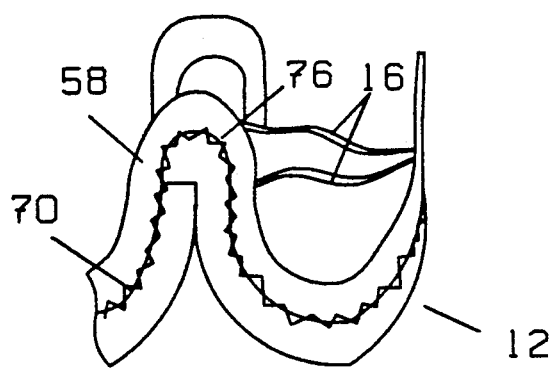
FIG. 15 is a perspective view of the frame with leaflets installed.

To prepare the annular ring 14 to receive the frame 12, tubular Dacron fabric 100, for example USCI bard tubular fabric, is wrapped around the ring 14 as shown in FIGS. 14 and 15. The tubular fabric 100 is stitched tight near a lower edge of the ring 14. At each of the commissure supports 48–52 a tab, 106, 108, 110 respectively, is attached. The tabs 106–110 are made of flat Dacron fabric and are stitched to the tubular Dacron fabric 100 at two points 112, 114 as shown in FIG. 17. A conventional sewing cuff 116 with silicon rubber insert can be placed around the base 42 of the frame. The leaflet assembly of FIG. 15 can now be set into the annular ring 14 of FIG. 18. The bias cut cloth 58 is wrapped over the upper edge 62 of the frame 12 and over the upper edge of the annular ring 14 and stitched to the ring. At the commissure tips, the cloth 58 is joined to the Dacron tabs 106–110. This method of attachment securely joins the frame 12 and the ring 14 so that the rigidity of the frame controls the motion of the lower third of the height of the commissures. The commissures are elastic in their upper portion. At the same time, the frame can shift circumferentially with respect to the ring to relieve temporary stresses.

Figure 19:
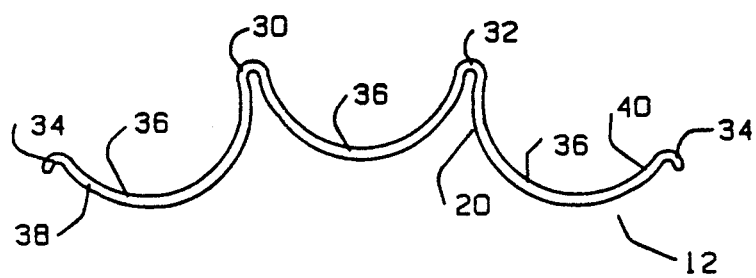
FIG. 19 is a plan view of a ribbon for forming the frame of FIG. 2.

The frame and the annular support ring cooperate to produce an artificial heart valve which approximates certain important features of a living biologic valve. One of the most important features which I have tried to reproduce is the stress-strain relationship characteristic of living tissue. I will explain this with reference to an idealized stress-strain curve illustrated in FIG. 21. As can be seen in FIG. 21, there is an initial portion 132 of a stress-strain curve 130 which has a very low slope. This implies a material which would have a large amount of plastic deformation under a very low loading. After the initial portion 132, there is a knee 134 in the stress-strain curve where the curve rapidly changes from a low slope to a high slope portion 136. In the high slope portion, the material characterized by the curve would not deform substantially despite increasing load. The kind of stress-strain curve illustrated in FIG. 19 is characteristic of living tissue and, in particular, of cardiac valve tissue. Previous heart valves have not had this kind of stress-strain curve. Rather, they have had a relatively constant linear stress-strain relationship in the heart valves. My invention produces an effective stress-strain relationship which more closely approximates the stress-strain curve of living biological material.

I call this an effective stress-strain curve because it does not represent the actual stresses and strains in any particular part of the valve, but rather represents the overall functioning of the valve taken as a whole. To cause the load in the leaflets to approach the natural level, the action of the frame and the annular ring are used. Taking the initial position of a tip of a commissure as a point of reference, the motion of the leaflets during the first part of an opening cycle for the valve rapidly displaces the tip of the commissure away from its initial position and toward the axis of the valve. In my design, there is almost no load taken by the commissure. Although the leaflets themselves are not deforming, their ends 72, 74 are being displaced away from the initial position of the tips of the commissures. This has the same effect as the low slope portion of the stress-strain curve 132 or a low spring constant. As the opening cycle continues, the Dacron tabs 106–110 are placed in tension and the leaflets are supported primarily by the relatively rigid annular frame and its commissure supports. There is still some flexibility available in the materials of the valve, characteristic of a high spring constant, so the stress-strain curve does not become vertical. Effectively, this reproduces a stress-strain curve which approximates the biologic curve shown in FIG. 21.

Figure 18:
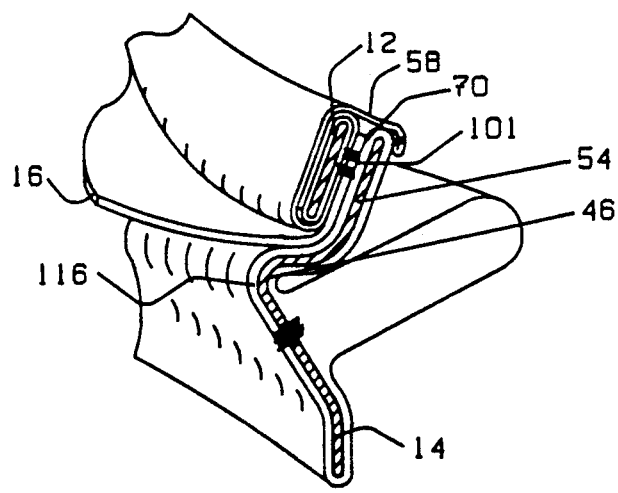
FIG. 18 is a partial through section of the assembled bioprosthetic heart valve taken along line 18—18 of FIG. 1.

The stresses on the edges of the leaflets 16 can be understood with reference to FIG. 18. When the valve 10 opens, the leaflets 16 are bent upwards and the leaflets 16 are wrapped around the frame 12. This distributes the stresses so that the load is taken both by the upper portion of the frame and by the stitches 70. However, since the leaflets 16 are bent back on themselves through more than 90°, most of the load will be borne by the frame 12 and cushioned by both the ribbon 56 and the cloth 58.

My invention may be embodied in other specific forms without departing from the spirit or essential characteristics thereof. The present embodiment is therefore considered in all respects to be illustrative and not restrictive, the scope of the invention being indicated by the appended claims rather than by the foregoing description and all changes which come within the meaning and range of equivalency of the claims are therefore intended to be embraced therein.

I claim as my invention:

1. A prosthetic heart valve comprising
   a generally annular elastic frame having a plurality of commissures extending generally axially and each commissure terminating at a distal end, each of said commissures being radially elastic over a portion of an axial length thereof, said elastic portion being adjacent said distal end;
   a generally annular, substantially rigid ring, said ring having commissure supports, each of said commissure supports extending along a second portion of one of said commissures, said second portion being remote from said distal end;
   valve leaflets attached to said frame and connecting adjacent commissures; and
   means for transferring loads from said valve leaflets primarily to said elastic portions of said commissures during a first part of a cardiac cycle and primarily to said commissure supports and rigid ring during a second part of said cardiac cycle.

2. The prosthetic heart valve according to claim 1 further comprising a plurality of rigid ribs affixed to said elastic frame and extending along at least part of said second portion of said commissures, whereby said part of said second portion of said commissures is rendered substantially rigid.

3. The prosthetic heart valve according to claim 1 or 2 wherein the load transferring means comprise a flexible material connecting at least part of an upper edge of said rigid ring and at least part of an upper edge of said elastic frame and wherein said leaflets pass between said rigid ring and a lower edge of said elastic frame.

4. The prosthetic heart valve according to claim 3 wherein the load transferring means further comprise a plurality of flexible sheets each sheet connecting a top of one of said commissure supports to an adjacent commissure.

5. The prosthetic heart valve according to claim 4 wherein said annular elastic frame comprises a flexible ribbon.

6. The prosthetic heart valve according to claim 5 wherein said ribbon has a width greater than ten times a depth of said ribbon.

7. The prosthetic heart valve according to claim 1 or 2 wherein at least part of a border of each of said valve leaflets lies between said frame and said ring.

8. The prosthetic heart valve according to claim 7 wherein said valve leaflets are attached to said frame near a first edge side of said elastic frame and wherein said border of each of said leaflets passes between said frame and said ring to a second edge of said frame.

9. The prosthetic heart valve according to claim 8 wherein said annular elastic frame comprises a flexible ribbon having a wide side at least part of which lies adjacent said annular ring and wherein said annular ring further comprises a channel adapted to mate with said wide side of said ribbon.

10. The prosthetic heart valve according to claim 9 wherein the annular ring further comprises a prominence adapted to conform to said second edge of said frame and proximal thereto.

11. The prosthetic heart valve according to claim 10 further comprising means for connecting said first edge of said frame to a distal edge of said rigid ring.

12. The prosthetic heart valve according to claim 11 wherein said valve leaflets further comprise a free edge connecting two adjacent commissures, said free edge being convex with respect to a line connecting a first junction between said free edge and one of said adjacent commissures and a second junction between said free edge and the other of said adjacent commissures.

13. The prosthetic heart valve according to claim 12 wherein said valve leaflets further comprise a fillet at each junction between said free edge and a commissure.

14. The prosthetic heart valve according to claim 13 wherein each of said commissures further comprise two adjacent interior edges, said edges being spaced a predetermined distance apart at a location adjacent said distal end and tapering towards each other away from said distal end to a second smaller distance and wherein a portion of the boarder of two adjacent leaflets are engaged between said adjacent interior edges.

15. A prosthetic heart valve comprising
   a generally annular frame having a plurality of commissures extending generally axially and distally thereof;
   a generally annular rigid base proximal of said frame and adjoining at least part of said frame, said frame comprising a distal edge, a proximal edge, and an outer side adjacent said base;
   valve leaflets attached to said frame, each valve leaflet connecting adjacent commissures and each leaflet having a border;
   at least part of said border of each of said valve leaflets lying between said frame and said base and attached to said frame near said distal edge of said frame and said border of said leaflets passing between said outer side of said frame and said base to said proximal edge of said frame and passing under a proximal edge of said frame, and
   means for connecting said distal edge of said frame to a distal edge of said rigid base.

16. The prosthetic heart valve according to claim 15 wherein said annular base further comprises a channel adapted to conform to said outer side of said frame.

17. The prosthetic heart valve according to claim 16 wherein the annular base further comprises a prominence adapted to conform to said proximal edge of said frame and proximal thereto.

18. A prosthetic heart valve comprising
   a generally annular frame having a plurality of commissures joined thereto and extending generally axially therefrom; and
   valve leaflets attached to said frame and connecting adjacent commissures, each of said valve leaflets further comprising a free edge connecting two adjacent commissures, each of said free edges being convex with respect to a line connecting a junction between said free edge and one of said adjacent commissures and a junction between said free edge and the other of said adjacent commissures.

19. The prosthetic heart valve according to claim 20 wherein each of said valve leaflets further comprises a first fillet at said junction between said free edge and said one of said adjacent commissures and a second fillet at said junction between said free edge and the other of said adjacent commissures.

20. A prosthetic heart valve comprising a frame having a plurality of commissures extending generally axially, each commissure terminating at a distal end and comprising two adjacent interior edges, said edges being spaced a predetermined distance apart at a location adjacent said distal end and tapering towards each other away from said distal end to a second smaller distance and a plurality of leaflets, each leaflet connecting first and second adjacent commissures and having a border, a first portion of which is disposed between said edges of said first adjacent commissure and a second portion of which is disposed between said edges of said second adjacent commissure.

* * * * *